United States Patent
Dominguez et al.

(10) Patent No.: US 9,681,974 B2
(45) Date of Patent: Jun. 20, 2017

(54) INTRAGASTRIC IMPLANTS WITH COLLAPSIBLE FRAMES

(71) Applicant: Apollo Endosurgery, Inc., Austin, TX (US)

(72) Inventors: Zachary Dominguez, Santa Barbara, CA (US); Mitchell H. Babkes, Santa Clarita, CA (US); Justin Schwab, Santa Barbara, CA (US); Christopher S. Mudd, Keller, TX (US); Jason Metzner, Covington, WA (US)

(73) Assignee: Apollo Endosurgery US, Inc., Austin, TX (US)

( * ) Notice: Subject to any disclaimer, the term of this patent is extended or adjusted under 35 U.S.C. 154(b) by 103 days.

(21) Appl. No.: 14/519,692

(22) Filed: Oct. 21, 2014

(65) Prior Publication Data

US 2015/0094753 A1    Apr. 2, 2015

Related U.S. Application Data

(62) Division of application No. 13/272,131, filed on Oct. 12, 2011, now Pat. No. 8,864,840.
(Continued)

(51) Int. Cl.
*A61F 2/04* (2013.01)
*A61F 5/00* (2006.01)

(52) U.S. Cl.
CPC .......... *A61F 5/0036* (2013.01); *A61F 5/0003* (2013.01); *A61F 5/003* (2013.01);
(Continued)

(58) Field of Classification Search
CPC ........ A61F 2/04; A61F 5/0086; A61F 5/0089; A61F 5/00; A61F 5/0033; A61F 5/0036;
(Continued)

(56) References Cited

U.S. PATENT DOCUMENTS

| 1,702,974 A | 2/1929 | MacDonald |
| 2,087,604 A | 7/1937 | Mosher |

(Continued)

FOREIGN PATENT DOCUMENTS

| CN | 1250382 A | 4/2000 |
| CN | 2007027812 A2 | 4/2000 |

(Continued)

OTHER PUBLICATIONS

'Living With the Bib/BioEnterics Intragastric Balloon Program,' Inamed Health; 1-10 Patient Information Brochure; pp.; May 1, 2005.
(Continued)

*Primary Examiner* — Victor Nguyen
(74) *Attorney, Agent, or Firm* — Gordon & Jacobson, P.C.

(57) ABSTRACT

Transoral obesity treatment devices and related methods for operation thereof are described which occupy space within a stomach and/or stimulate the stomach wall. The transoral obesity treatment devices and related methods are intended to assist a patient in maintaining a healthy body weight. Features of the devices include insertion transorally and without invasive surgery, without associated patient risks of invasive surgery, and without substantial patient discomfort. The life span of these devices may be material-dependent upon long-term survivability within an acidic stomach, but is intended to last one year or longer. The devices have the capacity to vary in size and are desirably self-actuating in that they change shape and/or volume using internal motors or actuators. The changing character of the devices helps prevent the person's stomach from compensating for the implant, such as sometimes happens with static intragastric devices.

18 Claims, 7 Drawing Sheets

Related U.S. Application Data

(60) Provisional application No. 61/485,009, filed on May 11, 2011, provisional application No. 61/394,592, filed on Oct. 19, 2010.

(52) U.S. Cl.
CPC .......... *A61F 5/0013* (2013.01); *A61F 5/0033* (2013.01); *A61F 5/0076* (2013.01); *A61F 5/0086* (2013.01); *A61F 5/0079* (2013.01); *A61F 5/0089* (2013.01); *Y10T 24/4453* (2015.01); *Y10T 24/44342* (2015.01); *Y10T 24/44564* (2015.01)

(58) Field of Classification Search
CPC .......... A61F 5/0079; A61F 5/003; A61F 2/00; A61B 19/00
See application file for complete search history.

(56) References Cited

U.S. PATENT DOCUMENTS

| | | |
|---|---|---|
| 2,163,048 A | 6/1939 | McKee |
| 2,619,138 A | 11/1952 | Marler |
| 3,667,081 A | 6/1972 | Burger |
| 3,719,973 A | 3/1973 | Bell |
| 3,840,018 A | 10/1974 | Heifetz |
| 3,919,724 A | 11/1975 | Sanders |
| 4,118,805 A | 10/1978 | Reimels |
| 4,364,379 A | 12/1982 | Finney |
| 4,416,267 A | 11/1983 | Garren |
| 4,430,392 A | 2/1984 | Kelley |
| 4,485,805 A | 12/1984 | Foster |
| 4,545,367 A | 10/1985 | Tucci |
| 4,586,501 A | 5/1986 | Claracq |
| 4,592,355 A | 6/1986 | Antebi |
| 4,598,699 A | 7/1986 | Garren |
| 4,607,618 A | 8/1986 | Angelchik |
| 4,636,213 A | 1/1987 | Pakiam |
| 4,648,383 A | 3/1987 | Angelchik |
| 4,694,827 A | 9/1987 | Weiner |
| 4,723,547 A | 2/1988 | Kullas |
| 4,739,758 A | 4/1988 | Lai |
| 4,773,432 A | 9/1988 | Rydell |
| 4,774,956 A | 10/1988 | Kruse |
| 4,844,068 A | 7/1989 | Arata |
| 4,881,939 A | 11/1989 | Newman |
| 4,899,747 A | 2/1990 | Garren |
| 4,925,446 A | 5/1990 | Garay |
| 4,930,535 A | 6/1990 | Rinehold |
| 4,950,258 A | 8/1990 | Kawai |
| 4,969,899 A | 11/1990 | Cox |
| 5,074,868 A | 12/1991 | Kuzmak |
| 5,084,061 A | 1/1992 | Gau |
| 5,211,371 A | 5/1993 | Coffee |
| 5,226,429 A | 7/1993 | Kuzmak |
| 5,255,690 A | 10/1993 | Keith |
| 5,259,399 A | 11/1993 | Brown |
| 5,289,817 A | 3/1994 | Williams |
| 5,308,324 A | 5/1994 | Hammerslag |
| 5,312,343 A | 5/1994 | Krog |
| 5,449,368 A | 9/1995 | Kuzmak |
| 5,514,176 A | 5/1996 | Bosley |
| 5,527,340 A | 6/1996 | Vogel |
| 5,540,701 A | 7/1996 | Sharkey |
| 5,547,458 A | 8/1996 | Ortiz |
| 5,601,604 A | 2/1997 | Vincent |
| 5,658,298 A | 8/1997 | Vincent |
| 5,693,014 A | 12/1997 | Abele |
| 5,725,507 A | 3/1998 | Petrick |
| 5,748,200 A | 5/1998 | Funahashi |
| 5,776,160 A | 7/1998 | Pasricha |
| 5,819,749 A | 10/1998 | Lee |
| 5,820,584 A | 10/1998 | Crabb |
| RE36,176 E | 3/1999 | Kuzmak |
| 5,938,669 A | 8/1999 | Klaiber |
| 6,074,341 A | 6/2000 | Anderson |
| 6,102,678 A | 8/2000 | Peclat |
| 6,102,897 A | 8/2000 | Lang |
| 6,102,922 A | 8/2000 | Jakobsson |
| 6,152,922 A | 11/2000 | Ouchi |
| 6,183,492 B1 | 2/2001 | Hart |
| 6,264,700 B1 | 7/2001 | Kilcoyne |
| 6,290,575 B1 | 9/2001 | Shipp |
| 6,322,538 B1 | 11/2001 | Elbert |
| 6,450,946 B1 | 9/2002 | Forsell |
| 6,454,699 B1 | 9/2002 | Forsell |
| 6,454,785 B2 | 9/2002 | De Hoyos Garza |
| 6,464,628 B1 | 10/2002 | Forsell |
| 6,470,892 B1 | 10/2002 | Forsell |
| 6,503,264 B1 | 1/2003 | Birk |
| 6,511,490 B2 | 1/2003 | Robert |
| 6,540,789 B1 | 4/2003 | Silverman |
| 6,547,801 B1 | 4/2003 | Dargent |
| 6,579,301 B1 | 6/2003 | Bales |
| 6,629,776 B2 | 10/2003 | Bell |
| 6,675,809 B2 | 1/2004 | Stack |
| 6,682,473 B1 | 1/2004 | Matsuura |
| 6,733,512 B2 | 5/2004 | McGhan |
| 6,733,513 B2 | 5/2004 | Boyle |
| 6,746,460 B2 | 6/2004 | Gannoe |
| 6,776,783 B1 | 8/2004 | Frantzen |
| 6,840,257 B2 | 1/2005 | Dario |
| 6,845,776 B2 | 1/2005 | Stack |
| 6,905,471 B2 | 6/2005 | Leivseth |
| 6,960,233 B1 | 11/2005 | Berg |
| 6,981,978 B2 | 1/2006 | Gannoe |
| 6,981,980 B2 | 1/2006 | Sampson |
| 6,994,095 B2 | 2/2006 | Burnett |
| 7,008,419 B2 | 3/2006 | Shadduck |
| 7,020,531 B1 | 3/2006 | Colliou |
| 7,033,384 B2 | 4/2006 | Gannoe |
| 7,037,344 B2 | 5/2006 | Kagan |
| 7,056,305 B2 | 6/2006 | Garza Alvarez |
| 7,090,699 B2 | 8/2006 | Geitz |
| 7,214,233 B2 | 5/2007 | Gannoe |
| 7,220,237 B2 | 5/2007 | Gannoe |
| 7,220,284 B2 | 5/2007 | Kagan |
| 7,223,277 B2 | 5/2007 | DeLegge |
| 7,320,696 B2 | 1/2008 | Gazi |
| 7,347,875 B2 | 3/2008 | Levine |
| 7,354,454 B2 | 4/2008 | Stack |
| 7,476,256 B2 | 1/2009 | Meade |
| 7,510,559 B2 | 3/2009 | Deem |
| 7,608,114 B2 | 10/2009 | Levine |
| 7,628,442 B1 | 12/2009 | Spencer |
| 7,682,330 B2 | 3/2010 | Meade |
| 7,695,446 B2 | 4/2010 | Levine |
| 7,699,863 B2 | 4/2010 | Marco |
| 7,753,870 B2 | 7/2010 | Demarais |
| 7,771,382 B2 | 8/2010 | Levine |
| 7,794,447 B2 | 9/2010 | Dann |
| 7,815,589 B2 | 10/2010 | Meade |
| 7,837,643 B2 | 11/2010 | Levine |
| 7,841,503 B2 | 11/2010 | Sonnenschein |
| 7,883,525 B2 | 2/2011 | DeLegge |
| 7,931,693 B2 | 4/2011 | Binmoeller |
| 7,981,162 B2 | 7/2011 | Stack |
| 8,029,455 B2 | 10/2011 | Stack |
| 8,032,223 B2 | 10/2011 | Imran |
| 8,075,582 B2 | 12/2011 | Lointier |
| 8,162,969 B2 | 4/2012 | Brister |
| 8,187,297 B2 | 5/2012 | Makower |
| 8,216,266 B2 | 7/2012 | Hively |
| 2002/0019577 A1 | 2/2002 | Arabia |
| 2002/0055757 A1 | 5/2002 | Torre |
| 2002/0095181 A1 | 7/2002 | Beyar |
| 2002/0139208 A1 | 10/2002 | Yatskov |
| 2002/0183782 A1 | 12/2002 | Tsugita |
| 2003/0045896 A1 | 3/2003 | Murphy |
| 2003/0073880 A1 | 4/2003 | Polsky |
| 2003/0074054 A1 | 4/2003 | Duerig |
| 2003/0100822 A1 | 5/2003 | Lew |
| 2003/0106761 A1 | 6/2003 | Taylor |
| 2003/0109935 A1 | 6/2003 | Geitz |

(56) References Cited

U.S. PATENT DOCUMENTS

| | | |
|---|---|---|
| 2003/0144575 A1 | 7/2003 | Forsell |
| 2003/0153905 A1 | 8/2003 | Edwards |
| 2003/0158570 A1 | 8/2003 | Ferrazzi |
| 2004/0044357 A1 | 3/2004 | Gannoe |
| 2004/0092892 A1 | 5/2004 | Kagan |
| 2004/0117031 A1 | 6/2004 | Stack |
| 2004/0122452 A1 | 6/2004 | Deem |
| 2004/0122453 A1 | 6/2004 | Deem |
| 2004/0143342 A1 | 7/2004 | Stack |
| 2004/0148034 A1 | 7/2004 | Kagan |
| 2004/0172142 A1 | 9/2004 | Stack |
| 2004/0186503 A1 | 9/2004 | DeLegge |
| 2005/0033332 A1 | 2/2005 | Burnett |
| 2005/0049718 A1 | 3/2005 | Dann |
| 2005/0055039 A1 | 3/2005 | Burnett |
| 2005/0085923 A1 | 4/2005 | Levine |
| 2005/0096692 A1 | 5/2005 | Linder |
| 2005/0110280 A1 | 5/2005 | Guy |
| 2005/0131485 A1 | 6/2005 | Knudson |
| 2005/0190070 A1 | 9/2005 | Rudduck |
| 2005/0192614 A1 | 9/2005 | Binmoeller |
| 2005/0192615 A1 | 9/2005 | Torre |
| 2005/0197714 A1 | 9/2005 | Sayet |
| 2005/0228504 A1 | 10/2005 | Demarais |
| 2005/0240279 A1 | 10/2005 | Kagan |
| 2005/0250979 A1 | 11/2005 | Coe |
| 2005/0256533 A1 | 11/2005 | Roth |
| 2005/0261711 A1 | 11/2005 | Okada |
| 2005/0267595 A1 | 12/2005 | Chen |
| 2005/0267596 A1 | 12/2005 | Chen |
| 2005/0273060 A1 | 12/2005 | Levy |
| 2005/0277975 A1 | 12/2005 | Saadat |
| 2006/0020278 A1 | 1/2006 | Burnett |
| 2006/0025799 A1 | 2/2006 | Basu |
| 2006/0069403 A1 | 3/2006 | Shalon |
| 2006/0106288 A1 | 5/2006 | Roth |
| 2006/0142700 A1 | 6/2006 | Sobelman |
| 2006/0178691 A1 | 8/2006 | Binmoeller |
| 2006/0190019 A1 | 8/2006 | Gannoe |
| 2006/0217762 A1 | 9/2006 | Maahs |
| 2006/0229702 A1 | 10/2006 | Agnew |
| 2006/0252983 A1 | 11/2006 | Lembo |
| 2007/0010864 A1 | 1/2007 | Dann |
| 2007/0016262 A1 | 1/2007 | Gross |
| 2007/0021761 A1 | 1/2007 | Phillips |
| 2007/0078476 A1 | 4/2007 | Hull |
| 2007/0083224 A1 | 4/2007 | Hively |
| 2007/0100368 A1 | 5/2007 | Quijano |
| 2007/0118168 A1 | 5/2007 | Lointier |
| 2007/0135803 A1 | 6/2007 | Belson |
| 2007/0135829 A1 | 6/2007 | Paganon |
| 2007/0147170 A1 | 6/2007 | Hood |
| 2007/0149994 A1 | 6/2007 | Sosnowski |
| 2007/0156013 A1 | 7/2007 | Birk |
| 2007/0156248 A1 | 7/2007 | Marco |
| 2007/0173881 A1 | 7/2007 | Birk |
| 2007/0185374 A1 | 8/2007 | Kick |
| 2007/0239284 A1 | 10/2007 | Skerven |
| 2007/0250020 A1* | 10/2007 | Kim ................. A61F 5/003 604/264 |
| 2007/0265598 A1 | 11/2007 | Karasik |
| 2007/0276428 A1 | 11/2007 | Haller |
| 2007/0288033 A1 | 12/2007 | Murature |
| 2007/0293716 A1 | 12/2007 | Baker |
| 2008/0015618 A1 | 1/2008 | Sonnenschein |
| 2008/0058840 A1 | 3/2008 | Albrecht |
| 2008/0058887 A1 | 3/2008 | Griffin |
| 2008/0065122 A1 | 3/2008 | Stack |
| 2008/0071305 A1 | 3/2008 | DeLegge |
| 2008/0097513 A1 | 4/2008 | Kaji |
| 2008/0167606 A1 | 7/2008 | Dann |
| 2008/0172079 A1 | 7/2008 | Birk |
| 2008/0208240 A1 | 8/2008 | Paz |
| 2008/0208241 A1 | 8/2008 | Weiner |
| 2008/0221595 A1 | 9/2008 | Surti |
| 2008/0228205 A1 | 9/2008 | Sharkey |
| 2008/0234718 A1 | 9/2008 | Paganon |
| 2008/0234834 A1 | 9/2008 | Meade |
| 2008/0243071 A1 | 10/2008 | Quijano |
| 2008/0243166 A1 | 10/2008 | Paganon |
| 2008/0249635 A1 | 10/2008 | Weitzner |
| 2008/0255601 A1 | 10/2008 | Birk |
| 2008/0255678 A1 | 10/2008 | Cully |
| 2008/0262529 A1 | 10/2008 | Jacques |
| 2008/0306506 A1 | 12/2008 | Leatherman |
| 2009/0012553 A1 | 1/2009 | Swain |
| 2009/0082644 A1 | 3/2009 | Li |
| 2009/0093767 A1 | 4/2009 | Kelleher |
| 2009/0093837 A1 | 4/2009 | Dillon |
| 2009/0131968 A1 | 5/2009 | Birk |
| 2009/0132031 A1 | 5/2009 | Cook |
| 2009/0149879 A1 | 6/2009 | Dillon |
| 2009/0177215 A1 | 7/2009 | Stack |
| 2009/0187206 A1* | 7/2009 | Binmoeller et al. .......... 606/191 |
| 2009/0198210 A1 | 8/2009 | Burnett |
| 2009/0216337 A1 | 8/2009 | Egan |
| 2009/0259246 A1 | 10/2009 | Eskaros |
| 2009/0275973 A1 | 11/2009 | Chen |
| 2009/0287231 A1 | 11/2009 | Brooks |
| 2009/0299327 A1 | 12/2009 | Tilson |
| 2009/0299486 A1 | 12/2009 | Shohat |
| 2009/0312597 A1 | 12/2009 | Bar |
| 2010/0030017 A1 | 2/2010 | Baker |
| 2010/0049224 A1 | 2/2010 | Vargas |
| 2010/0081991 A1 | 4/2010 | Swisher |
| 2010/0082047 A1 | 4/2010 | Cosgrove |
| 2010/0087843 A1 | 4/2010 | Bertolote |
| 2010/0100079 A1 | 4/2010 | Berkcan |
| 2010/0100115 A1 | 4/2010 | Soetermans |
| 2010/0121371 A1 | 5/2010 | Brooks |
| 2010/0168782 A1 | 7/2010 | Hancock |
| 2010/0168783 A1 | 7/2010 | Murature |
| 2010/0174307 A1 | 7/2010 | Birk |
| 2010/0198249 A1 | 8/2010 | Sabliere |
| 2010/0234937 A1 | 9/2010 | Wang |
| 2010/0249822 A1 | 9/2010 | Nihalani |
| 2010/0249825 A1 | 9/2010 | Nihalani |
| 2010/0256775 A1 | 10/2010 | Belhe |
| 2010/0256776 A1 | 10/2010 | Levine |
| 2010/0261390 A1 | 10/2010 | Gardner |
| 2010/0274194 A1 | 10/2010 | Sobelman |
| 2010/0286628 A1 | 11/2010 | Gross |
| 2010/0305590 A1 | 12/2010 | Holmes |
| 2010/0331756 A1 | 12/2010 | Meade |
| 2010/0332000 A1 | 12/2010 | Forsell |
| 2011/0009897 A1 | 1/2011 | Forsell |
| 2011/0106113 A1 | 5/2011 | Tavakkolizadeh |
| 2011/0307075 A1 | 12/2011 | Sharma |
| 2012/0022561 A1 | 1/2012 | Forsell |
| 2012/0095483 A1 | 4/2012 | Babkes |
| 2012/0221037 A1 | 8/2012 | Birk |

FOREIGN PATENT DOCUMENTS

| | | |
|---|---|---|
| CN | 1367670 A | 9/2002 |
| CN | 2007053556 A1 | 9/2002 |
| DE | 8804765 U1 | 6/1989 |
| DE | 2007076021 A2 | 6/1989 |
| DE | 102007025312 A1 | 11/2008 |
| EP | 1396242 | 3/2004 |
| EP | 1396243 | 3/2004 |
| EP | 1397998 A1 | 3/2004 |
| EP | 2007092390 A2 | 3/2004 |
| EP | 1774929 A2 | 4/2007 |
| EP | 2095798 | 9/2009 |
| FR | 2797181 | 2/2001 |
| FR | 2008101048 A2 | 2/2001 |
| FR | 2823663 | 10/2002 |
| FR | 2008112894 A1 | 10/2002 |
| FR | 2852821 A1 | 10/2004 |
| FR | 2008132745 A2 | 10/2004 |
| FR | 2855744 | 12/2004 |
| FR | 2892297 A1 | 4/2007 |
| FR | 2941617 A1 | 8/2010 |

(56) References Cited

FOREIGN PATENT DOCUMENTS

| | | | |
|---|---|---|---|
| GB | 2086792 | A | 5/1982 |
| GB | 2010074712 | A2 | 5/1982 |
| JP | 63264078 | | 10/1988 |
| JP | 2006111961 | A2 | 10/1988 |
| JP | 2010117641 | A2 | 11/1988 |
| JP | S63279854 | A | 11/1988 |
| JP | 1049572 | A | 2/1989 |
| JP | 2010087757 | A1 | 2/1989 |
| WO | 8800027 | | 1/1988 |
| WO | 0015158 | | 3/2000 |
| WO | 0032092 | | 6/2000 |
| WO | 0110359 | | 2/2001 |
| WO | 0149245 | | 7/2001 |
| WO | 0166166 | A2 | 9/2001 |
| WO | 0235980 | A2 | 5/2002 |
| WO | 03055419 | A1 | 7/2003 |
| WO | 03105732 | | 12/2003 |
| WO | 2004019671 | A2 | 3/2004 |
| WO | 2005007231 | A1 | 1/2005 |
| WO | 2005094257 | A2 | 10/2005 |
| WO | 2005097012 | A2 | 10/2005 |
| WO | 2005110280 | A2 | 11/2005 |
| WO | 2006020370 | | 2/2006 |
| WO | 2006044640 | A1 | 4/2006 |
| WO | 8800027 | A1 | 6/2006 |
| WO | 2006063593 | A2 | 6/2006 |
| WO | 2006090018 | A1 | 8/2006 |
| WO | 2006118744 | A1 | 11/2006 |
| WO | 2007110866 | A2 | 10/2007 |
| WO | 2010042062 | A1 | 4/2010 |

OTHER PUBLICATIONS

Baggio et al. 'Biology of Integrins: GLP-1 and GIP'; Gastroenterology; V. 132; pp. 2131-2157; 2007.
Berne et al; 'Physiology'; V. 5; pp. 55-57, 210, 428, 540, 554, 579, 584, 591; 2004.
BIB Bioenterics Intragastric Balloon Program, 'Take Control of Your Weight and Your Life/The Solution for You,' Inamed Health, pp. 1-2; Jan. 19, 2004.
BIB Bioenterics Intragastric Balloon Program, 'Taking the Next Step/Take Control of Your Weight and Your Life,' Inamed Health, pp. 1-9; Apr. 29, 2004.
BIB Data Sheet Directions for Use, 'BioEnterics Intragastric Balloon System,' Inamed Health, 1-12 pp.
Boulant et al.; 'Cholecystokinin in Transient Lower Oesophageal Sphincter Relation Due to Gastric Distension in Humans'; Gut; V. 40; pp. 575-581; 1997.
Bradjewin et al; 'Dose Ranging Study of the Effects of Cholecystokinin in Healthy Volunteers'; J. Psychiatr. Neurosci.; V. 16 (2); pp. 91-95; 1991.
Chaudhri; 'Can Gut Hormones Control Appetite and Prevent Obesity?' Diabetes Care; V. 31; Supp 2; pp. S284-S289; Feb. 2008.
Cohen et al.; 'Oxyntomodulin Suppresses Appetite and Reduces Food Intake in Humans'; J. Clin. Endocrinol. Metab.; V. 88; No. 10; pp. 4696-4701; 2003.
Dakin et al.; 'Oxyntomodulin Inhibits Food Intake in the Rat'; Endocrinology; V. 142; No. 10; pp. 4244-4250; 2001.
Dakin et al.; 'Peripheral Oxyntomodulin Reduces Food Intake and Body Weight gain in Rats'; Endocrinology; V. 145; No. 6; pp. 2687-2695; Jun. 2004.
Davison; 'Activation of Vagal-Gastric Mechanoreceptors by Cholecystokinin'; Proc. West. Pharmocol. Soc; V. 29; pp. 363-366; 1986.
Ekblad et al.; 'Distribution of Pancreatic Peptide and Peptide-YY'; Peptides; V. 23; pp. 251-261;2002.
Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Houpt; 'Gastrointestinal Factors in Hunger and Satiety'; Neurosci. and Behav. Rev.; V. 6; pp. 145-164; 1982.
Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.
Naslund et al. 'Pranidal subcutaneous injections of glucagon-like peptide-1 cause weight loss in obese human subjects'; British Journal of Nutrition; V. 91; pp. 439-446; 2004.
Renshaw et al. 'Peptide YY: A Potential Therapy for Obesity'; Current Drug Targets; V. 6; pp. 171-179; 2005.
Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.
Wynne et al.; 'Subcutaneous Oxyntomodulin Reduces Body Weight in Overweight and Obese Subiects: A Double-Blind Randomized, Controlled Trial': Diabetes; V. 54; pp. 2390-2395; 2005.
Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

* cited by examiner

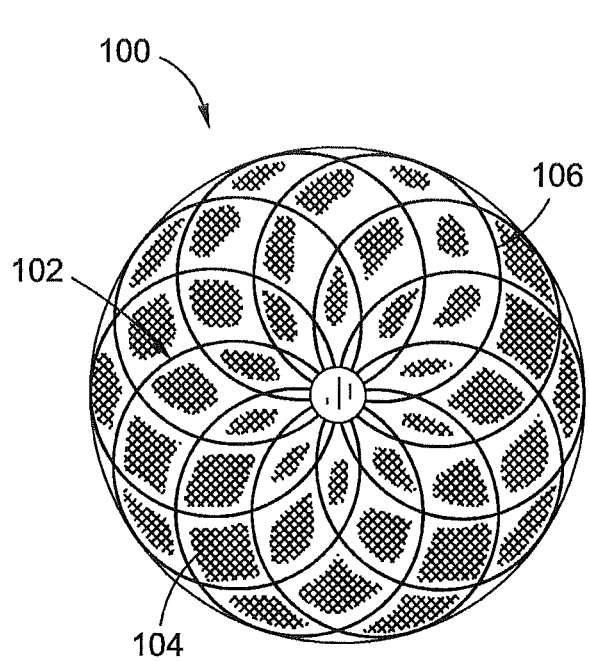
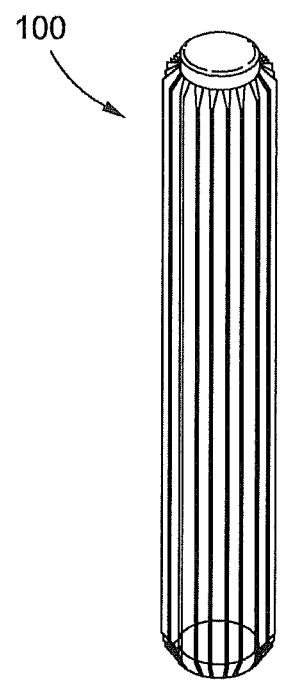
FIG. 3     FIG. 4
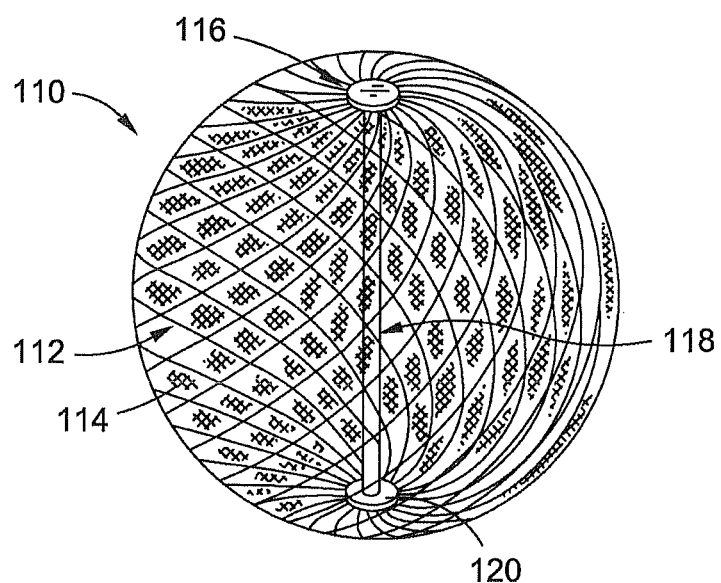
FIG. 5

INTRAGASTRIC IMPLANTS WITH COLLAPSIBLE FRAMES

RELATED APPLICATIONS

The application is a divisional of U.S. Ser. No. 13/272,131, filed Oct. 12, 2011, and now issued as U.S. Pat. No. 8,864,840, which claims priority under 35 U.S.C. §119 to U.S. Provisional Application No. 61/485,009, filed May 11, 2011, and to 61/394,592, filed Oct. 19, 2010, the disclosures of all of which are incorporated by reference herein in their entireties.

FIELD OF THE INVENTION

The present invention generally relates to medical implants and uses thereof for treating obesity and/or obesity-related diseases and, more specifically, to transorally-delivered devices designed to occupy space within a stomach and/or stimulate the stomach wall.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States was estimated to be about 400,000 in 2010.

Examples of surgical methods and devices used to treat obesity include the LAP-BAND® (Allergan, Inc., Irvine, Calif.) gastric band and the LAP-BAND AP® (Allergan, Inc., Irvine, Calif.). However, surgery might not be an option for every obese individual; for certain patients, non-surgical therapies or minimal-surgery options are more effective or appropriate.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These devices are designed to provide therapy for moderately obese individuals who need to shed pounds in preparation for surgery, or as part of a dietary or behavioral modification program. These balloons are typically cylindrical or pear-shaped, generally range in size from 200-500 ml or more, are made of an elastomer such as silicone, polyurethane, or latex, and are filled with air, an inert gas, water, or saline.

One such inflatable intragastric balloon is described in U.S. Pat. No. 5,084,061 and is commercially available as the BioEnterics Intragastric Balloon System ("BIB System," sold under the trademark ORBERA). The BIB System comprises a silicone elastomer intragastric balloon that is inserted into the stomach and filled with fluid. Conventionally, the balloons are placed in the stomach in an empty or deflated state and thereafter filled (fully or partially) with a suitable fluid. The balloon occupies space in the stomach, thereby leaving less room available for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Placement of such balloons is temporary, and such balloons are typically removed after about six months. Removing the balloon requires deflation by puncturing with a gastroscopic instrument, and either aspirating the contents of the balloon and removing it, or allowing the fluid to pass into the patient's stomach. Clinical results with these devices show that for many obese patients, the intragastric balloons significantly help to control appetite and accomplish weight loss.

Despite the advances in the design of intragastric balloons, there remains a need for improved transoral obesity treatment devices.

SUMMARY OF THE INVENTION

Transoral obesity treatment devices generally promote a feeling of satiety in the patient by contacting the insides of the stomach wall, reducing the space in the stomach, or otherwise reducing the amount of food consumed or digested by the patient.

In accordance with one embodiment, an intragastric obesity treatment implant disclosed herein comprises a collapsible/expandable frame formed of a plurality of spaced struts, the frame having a relaxed generally spherical configuration with a size sufficient to contact the interior stomach walls upon contraction thereof. A flexible material drapes around and connects to the frame so as to span across the spaces between the struts. The frame is capable of being converted into a substantially linear delivery configuration and being formed of a material that will resist degradation over a period of at least six months within the stomach. The collapsible/expandable frame may comprise a plurality of circular wires interwoven to define a sphere when relaxed. In one embodiment, the circular wires all wind around the sphere in one direction, CW or CCW. In another form, the collapsible/expandable frame comprises an articulated frame of a plurality of strut elements connected together at joints and forming a plurality of struts that extend from a pole of the sphere to an opposite pole. The flexible material may be a porous mesh or may be impermeable and the implant is filled with saline. Desirably, the shape of the collapsible/expandable frame is adjustable in vivo.

Another intragastric obesity treatment implant includes a collapsible/expandable frame formed of a plurality of spaced wires each extending between end poles along a generally helical path. The frame has a relaxed generally spherical configuration with a size sufficient to contact the interior stomach walls upon contraction thereof. The frame is also capable of being converted into a substantially linear delivery configuration by displacing the poles away from one another, and is formed of a material that will resist degradation over a period of at least six months within the stomach. The implant may further have a flexible material draped around and connected to the frame so as to span across the spaces between the wires, such as a porous mesh or an impermeable material such that the implant may be filled with saline. The helical wires may all wind around the sphere in one direction between the end poles, CW or CCW, or in both directions to form a braided mesh. The shape of the collapsible/expandable frame is preferably adjustable in vivo. In one embodiment, the wires are Nitinol and the ends of the wires are held by end caps of silicones.

A still further intragastric obesity treatment implant of the present application comprises a plurality of collapsible/expandable frames formed of a plurality of spaced struts having a relaxed generally spherical configuration. The frames are connected in series with intermediate tethers, and each frame has a size that will not pass through the pyloric sphincter and is made of a material that will resist degradation over a period of at least six months within the stomach. A duodenal anchor connected to a distal frame may be included, the duodenal anchor having a size that permits it to pass through the pyloric sphincter and be formed of a material of sufficient mass and specific gravity that prevents it from migrating back up through the pyloric sphincter. A proximal frame may include an internally threaded sleeve suitable for receiving an externally threaded end of a delivery tube, and the intermediate tethers are preferably tubular permitting passage of a stiff rod through the series of frames. In addition, a flexible material draped may be draped around and connected to each frame so as to span across the spaces between the struts.

BRIEF DESCRIPTION OF THE DRAWINGS

The following detailed descriptions are given by way of example, but not intended to limit the scope of the disclosure solely to the specific embodiments described herein, may best be understood in conjunction with the accompanying drawings in which:

FIG. 3 is a plan view from above of an exemplary spherical draped wireframe structure for use as an intragastric device;

FIG. 4 is a perspective view of the device of FIG. 3 collapsed into an elongated delivery configuration;

FIG. 5 is a perspective view of a draped wireform intragastric device similar to that shown in FIG. 3 and having the ability to adjust the size of the device;

DESCRIPTION OF THE DETAILED EMBODIMENTS

Figure 1:
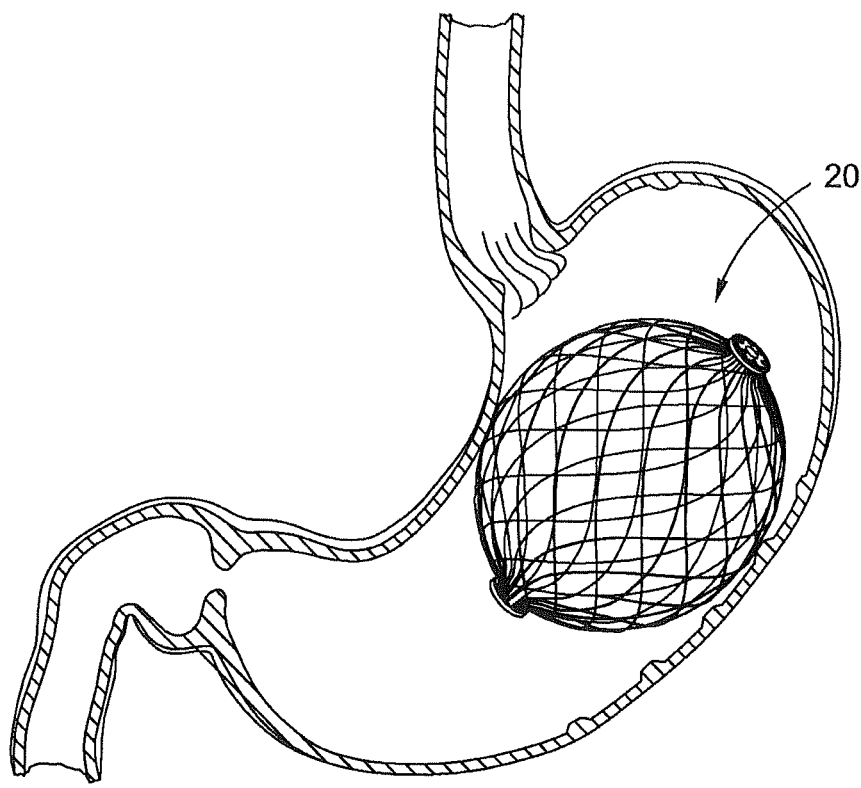
FIG. 1 is a sectional view through a human stomach illustrating a collapsible spherical frame implanted therein.

Persons skilled in the art will readily appreciate that various aspects of the disclosure may be realized by any number of methods and devices configured to perform the intended functions. Stated differently, other methods and devices may be incorporated herein to perform the intended functions. It should also be noted that the drawing Figures referred to herein are not all drawn to scale, but may be exaggerated to illustrate various aspects of the invention, and in that regard, the drawing Figures should not be construed as limiting. Finally, although the present disclosure may be described in connection with various medical principles and beliefs, the present disclosure should not be bound by theory.

By way of example, the present disclosure will reference certain transoral obesity treatment devices. Nevertheless, persons skilled in the art will readily appreciate that certain aspects of the present disclosure advantageously may be applied to one of the numerous varieties of transoral obesity treatment devices other than those disclosed herein.

In one aspect, these transoral obesity treatment devices described herein are intended to be placed inside the patient, transorally and without invasive surgery, without associated patient risks of invasive surgery and without substantial patient discomfort. Recovery time may be minimal as no extensive tissue healing is required. The life span of these transoral obesity treatment devices may be material-dependent upon long-term survivability within an acidic stomach, but is intended to last one year or longer.

Figure 2:
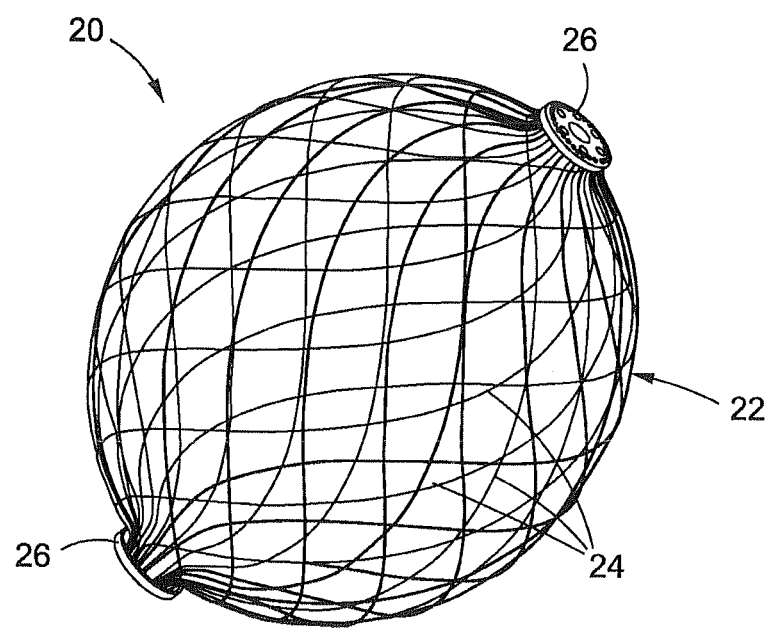
FIG. 2 is a perspective view of the device of FIG. 1.

In a first embodiment disclosed herein, FIGS. 1 and 2 show an intragastric implant 20 comprising a generally spherical collapsible frame 22. The frame 22 includes a plurality of individual wires 24 that each extend between and connect to opposite end caps 26. The end caps 26 define opposite poles of the collapsible frame 22 as well as a longitudinal axis therebetween. In a preferred embodiment, there is no material draped across the frame, and fluid can freely flow between the wires in and out of the cavity defined therein. This "fluidless" or balloon-shaped non-inflatable structure thus serves to contact the inner stomach walls, thus stimulating nerves and inducing feelings of satiety. Due to the lack of inflation fluid, there is no danger of inadvertent deflation and passage into the lower gastrointestinal tract.

As seen in FIG. 1, the smaller size relative to the stomach permits the implant 20 to move around somewhat. In terms of size limits of the expanded (relaxed) implant 20, the diameter of the generally spherical frame 22 is greater than the size of the pyloric sphincter to ensure it will not pass through the lower gastrointestinal tract, but less than the minimum estimated width of the stomach cavity so that it can move around. For instance, the equatorial diameter of the implant 20 is between about 8-15 cm. As stated, the shape is desirably spherical, though some elongation along the axis may be acceptable to form a more prolate spheroid. Further, the shape may be adjustable such as with structure described below with reference to FIG. 5. An acceptable size ratio between the equatorial diameter and the dimension between the axial poles is between about 75-125%. Of course, when elongated for delivery or removal this ratio will be much lower. And in use, the stomach churning may deform the implant 20 from its equilibrium shape, to squish the poles together for instance, to result in a much higher ratio.

In one embodiment, the intragastric implant 20 includes an elastic frame 22 with substantially soft, atraumatic end caps 26. The wires 24 that make up the frame 22 may be metallic, such as Nitinol, or a polymer than can withstand the stomach environment for lengthy periods, preferably at least a year. Nitinol is preferred for its relatively inert behavior in the stomach chemistry, its extreme elasticity, and the relatively low frictional coefficient against itself. In one configuration, the wires 24 are coated with silicone to take advantage of its resistance to deterioration in the stomach as well as its lubricity. The end caps 26 desirably comprise a soft polymer such as silicone.

The implant 20 is designed to collapse into an elongated tube oriented axially with the caps 26 at each end. In one embodiment, alternating wires 24 of the elastic frame 22 are weaved in opposite generally helical paths to form a braided mesh. As shown, each wire 24 desirably attaches to one end cap 26 in a substantially axial orientation, and then curves into a generally helical path before transitioning back to an axial direction at the other end cap 26. Such a mesh can be elongated along the axis by displacing the end caps 26 apart to reduce the radial profile of the frame 22. For instance, a delivery tool (not shown) may engage one end cap 26 while passing a deployment probe through the middle of the frame 22 to the opposite end cap 26. Extension of the probe and distal end cap 26 while maintaining the position of the proximal end cap 26 pushes apart the two poles of the implant 20 and collapses the frame 22. Subsequent to delivery of the implant 20 into the stomach, the delivery tool releases both end caps 26 and the elasticity of the frame 22 causes it to expand into the generally spherical shape shown. Removal of the implant 20 occurs in the opposite way, with the tool grasping one end cap 26 and the deployment probe extending through the interior of the frame 22 to engage and distally displace the opposite end cap 26.

The expanded spherical shape shown represents the relaxed shape of the wires 24, at least within the constraints of the assembly between the end caps 26. Either bare Nitinol or Nitinol coated with silicone provides relatively low sliding friction between the wires, which facilitates both expansion on delivery and contraction at the time of removal. In a preferred embodiment, there are at least thirty total wires 24, and more preferably there are at least twenty helical wires 24 extending around the frame 22 in each rotational direction. Of course, other mesh patterns than the braided helical one shown are contemplated, such as described below, as long as the frame 22 can be easily expanded for delivery and contracted for removal.

FIGS. 3-9 disclose alternative intragastric, implantable devices to facilitate weight loss that comprise semi-rigid frames which can elastically deform in response to stomach contractions. The devices are designed such that they can collapse into an orientation that can be easily implanted and explanted transorally, through the esophagus, and into/out of the stomach during a minimally invasive gastroendoscopic procedure. The collapsible/expandable frames, wireframes, or articulated elements each consist of a geometrical configuration of struts that provide integrity to the device, yet are capable of some amount of flexibility and compliance. The structure is rigid enough such that the device maintains a generally spherical shape in situ. The frame inherently prevents migration out of the stomach throughout the duration of the implantation period. The deformation of the structure is intended to accommodate a range of stomach sizes/shapes and allow for some compressibility as the stomach contracts on it.

Each of the devices disclosed in FIGS. 3-9 desirably may be collapsed into a nearly cylindrical shape that permits implantation and explantation through the esophagus. While in this cylindrical, collapsed shape, the device maintains a degree of flexibility along its axis to facilitate navigation through the non-linear esophageal lumen.

Furthermore, the devices of FIGS. 3-9 may or may not be volume reducing. For example, in one embodiment a mesh fabric is draped around the collapsible/expandable frame. This would therefore not be volume reducing (because fluids could pass freely through mesh) but would exert more uniform pressure on the stomach walls. A semi-permeable covering has the added benefit of equilibrating with stomach pressures and no risk of deflation and loss of functionality. In another embodiment, the device would be draped with an impermeable membrane (e.g. silicone) and filled with either gas or liquid. This would also exert pressure on the stomach wall but would also be volume reducing.

In either embodiment, the flexible drape material serves to increase the surface area over which the structure acts on the stomach. The drape material is connected to the collapsible/expandable frame such as with sutures, adhesive or other expedient, or may be connected by virtue of surrounding and encapsulating the frame. Desirably, the devices provide in-vivo adjustability via endoscopic means. Symmetry of the spherical shape allows for multiple endoscopic access points, for easier navigation during in-vivo endoscopic adjustments. Finally, there is a reduced risk of the devices passing through the pylorus during the course of implantation. Even when collapsed, the frame provides enough bulk to prevent the device from passing from the stomach.

As mentioned, the devices may or may not allow material to enter the internal volume. If a mesh material is used, the device will exhibit a generally higher compliance than a device which contains a set volume of an incompressible fluid. If a fluid is used to fill the device, once must consider the added complexity of filling and emptying the device during implantation/explantation as well as the effects of the added mass within the stomach. Either approach is largely dependent on the biological mechanisms which drive satiety. If stimulation of the stomach walls is the intent, a device which does not reduce overall stomach volume (significantly) may be preferred. If the volume occupying characteristics of these types of devices is desired, a device which can be filled with a fluid is selected. The drape component may or may not be elastic. However, it is important the material be relatively compliant such that it takes the shape of the wireframe and generally conforms to the shape of the stomach (insomuch as the wireframe will allow).

FIG. 3 is a plan view of an intragastric device 100 having a wireframe 102 that expands to a spherical shape and is desirably draped with a flexible fabric 104. FIG. 4 shows the device 100 collapsed into an elongated tubular delivery configuration.

The core components of the device 100 are multiple wires 106 (or equivalent polymer fiber, e.g. PEEK) that gives the device its spherical shape. An exemplary embodiment uses Nitinol (NiTi, Nickel Titanium) due to the shape-memory characteristics of the material, but the wires 106 can be made of any material with properties equivalent to Nitinol. Each separate wire 106 of the wireframe 102 consists of a circle projected onto a spherical surface. This circular form is evident in the top-down perspective of FIG. 3. This projected circular shape of each wire 106 provides hoop strength to the structure when acted upon by a force. In contrast, if the wires were aligned longitudinally, from pole-to-pole, an outside lateral force might cause the individual wires to buckle, thus causing the structure to behave unpredictably. However, that same force acting on the circular wire configuration shown in the figures will tend to be "absorbed" by the structure as it elastically deforms into a more oval shape—the overall structure is not compromised. The ability to absorb compressive pressures cannot be understated, the stomach muscles constantly churn and are enormously strong, so resiliency of the structure is extremely important to avoid fracture or buckling.

The wireframe 102 may consist of wires 106 aligned in the same direction (clockwise vs. counter-clockwise) or both directions, and the total number of wires can be adjusted. A single orientation (CW vs. CCW) lends itself to easier collapse, however a dual orientation (CW and CCW) creates a more robust, braided structure. Note that if a dual direction (CW and CCW) approach is taken, consideration must be made regarding how the wires interact with each other at the intersection points when collapsing. A single direction approach makes this shape much more realistic. In this configuration, the device can be easily collapsed into a cylindrical form and passed through the esophagus during implantation and explantation procedures as it is allowed to flex slightly along its long axis. Many wires add to the complexity of the device, but give it a more spherical form, while fewer wires simplify the device, but create sharper "edges" where a draped fabric bends around the wires. Various examples are shown in FIGS. 6A-6F, described below.

FIG. 5 illustrates an alternative intragastric device 110 having a wireframe 112 draped with a fabric 114, similar to that shown in FIG. 3, but including the ability to adjust the size of the device. It should be noted that each embodiment disclosed in FIGS. 3-9 is meant to be endoscopically accessible for in-vivo adjustments of frame shape. Adjustability of device shape allows physicians to modify the geometry of the mechanical frame to prevent the patient's physiology from adapting to the presence of a volume occupation implant. That is, adjustability allows for intermittent shape modification to prevent the body from becoming accustomed to one shape, which might reduce efficacy of the device. Additionally, adjustability of a singular device reduces the risk of requiring repeated complete device removals for implantation of a different sized/shaped intragastric balloon. Adjustments would be performed by endoscopically accessing a feature on the design, such that the frame's default shape can be modified. Compliance will not change, but the default shape to which the frame will take will be reliant upon the adjustment performed.

In the embodiment of FIG. 5, the device 110 is provided within endoscopic access point 116 at one pole. A column 118 having movable concentric tubes (not shown) extends diametrically across the interior of the device 110 to a second pole 120. The individual wires of the wireframe 112 may be firmly connected to different tubes of the column 118 at the poles, which may then be relatively rotated to collapse the wireframe by winding the wires more tightly, or to expand the wireframe by causing them to unwind and separate. That is, winding the wires more tightly causes the device 110 to contract in size, while unwinding the wires causes the device to increase in diameter, even past a spherical configuration to flatten the structure. Alternatively, the draped fabric 114 may be fluid impermeable such that the device 110 may be inflated with saline. Adjustments in size may therefore be accomplished by injecting saline to increase the volume, and withdrawing saline to decrease the volume.

Figure 6A:
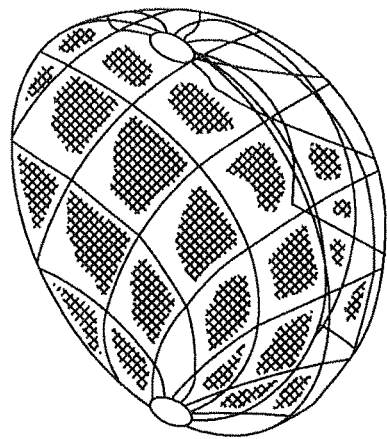
FIGS. 6A-6F are perspective cutaway views of variations on the draped wireform intragastric device of the present application.
Figure 6B:
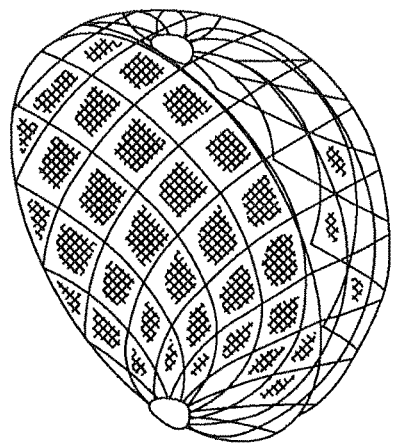
Figure 6C:
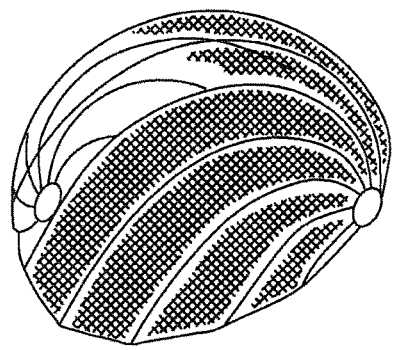
Figure 6D:
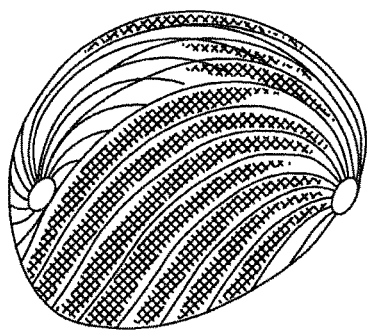
Figure 6E:
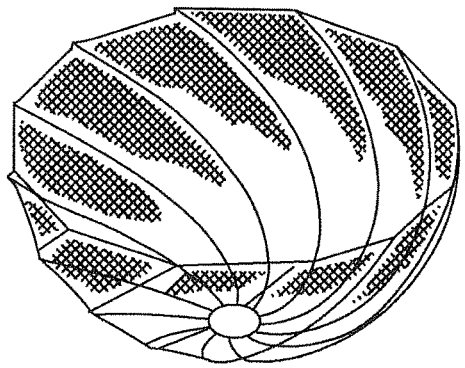
Figure 6F:
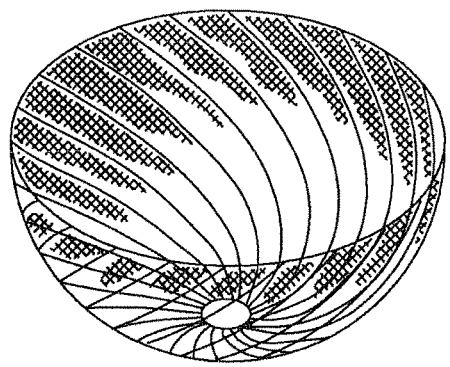

As mentioned, FIGS. 6A-6F illustrate variations on the draped wireform intragastric device of the present application. FIGS. 6A and 6B illustrate wires wound around the device in both CW and CCW orientations, with ten total in FIG. 6A and fifteen total in FIG. 6B. Twelve total wires and twenty-four total wires, respectively, are shown wound in a single orientation (CW) in FIGS. 6C and 6D. Finally, using horizontal sections through the equator of the device, twelve total wires and twenty-four total wires, respectively, wound in a single direction are shown in FIGS. 6F and 6F to illustrate the more polygonal configuration with less wires versus a more spherical result with more wires.

Figure 7:
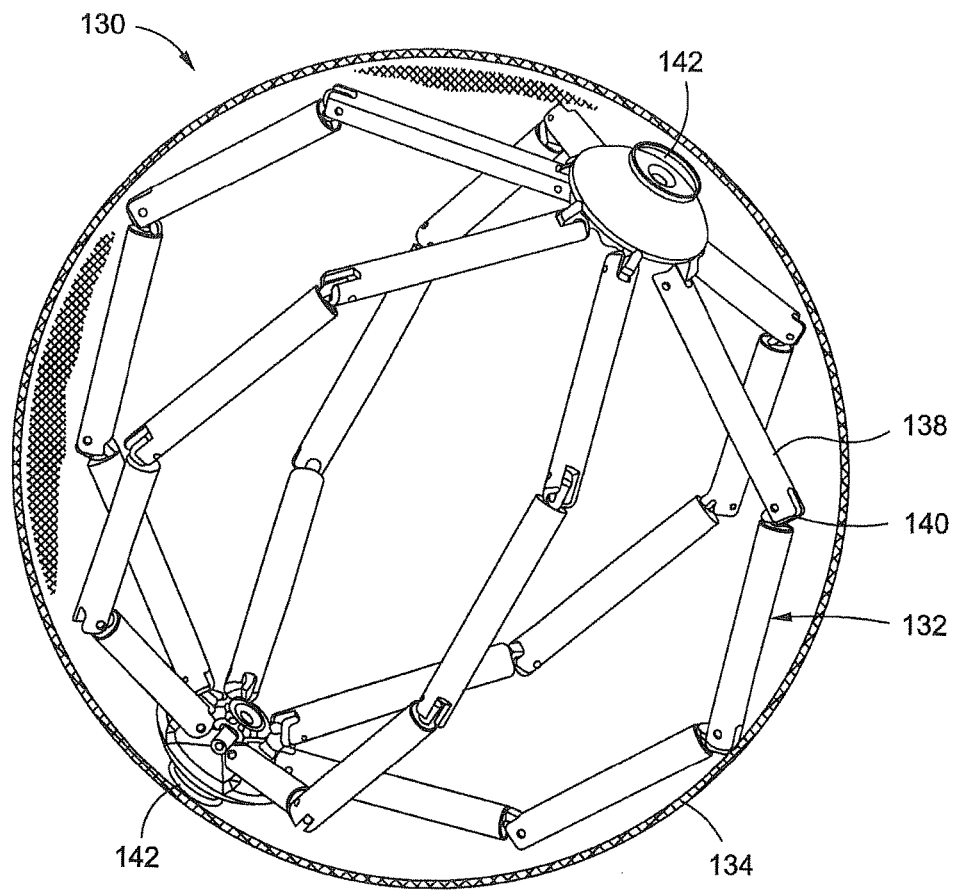
FIG. 7 is a perspective view of a spherical draped articulated frame intragastric device of the present application.
Figure 8A:
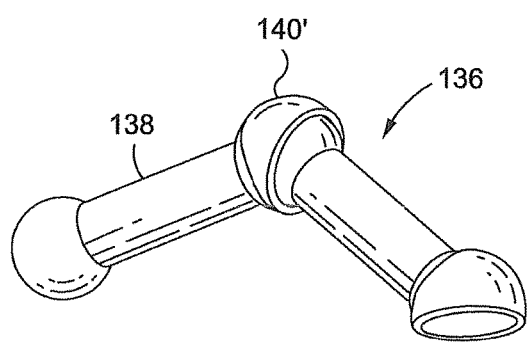
FIGS. 8A and 8B are enlarged perspective views of individual linkages for use with the draped articulated frame intragastric device of FIG. 7.
Figure 8B:
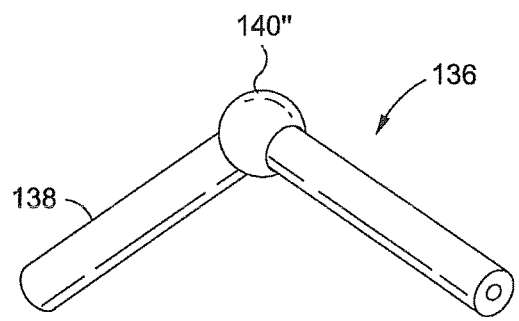

FIG. 7 is a perspective view of an alternative intragastric device 130 of the present application having an articulated frame 132 expanded in a spherical configuration and having a flexible fabric 134 draped thereover. In this context, "articulated" means that the frame 132 comprises a plurality of relatively stiff members connected at hinges. The core component of this device is a mechanized set of independently linked assemblies 136 comprising two strut elements 138 and a hinge 140, alternative examples of which are shown in FIGS. 8A and 8B. The entire articulated frame 132 desirably consists of between 6-12 struts in total converging at opposite poles 142. The poles 142 comprise end caps with a plurality of hinges linked to each converging strut element 138. In the illustrated embodiment, there are six struts comprising four strut elements 138 each, for a total of twenty-four independently-linked strut elements. The benefit of this mechanical structure is the inherent robustness of the individual segments, relying on the mechanics of their articulated interaction instead of material properties.

The intragastric device 130 illustrated features two primary access points for endoscopic adjustment. The strut elements 138 are preferably hollow tubes, and the device 130 desirably incorporates in-vivo adjustability via elements that run through the lumens of, or parallel with, the struts. These elements would then be accessed via points, such as at the poles 142, on the frame using an endoscopic accessory (not shown). For instance, flexible cables could run through the hollow strut elements 138 and through apertures in each hinge 140, whereby tightening the cables pulls the struts straight and vice versa.

The compliance and flexibility of the frame are directly related to the length and number of individual strut elements 138, and configuration of the hinges 140. FIG. 7 shows hinges 140 that limit articulation of adjacent strut elements 138 to within a single plane. Note that hinged joints limit flexibility in the collapsed form, but increase alignment within their pivot plane. Alternatively, FIG. 8A illustrates a ball, or rolling joint 140', while FIG. 8B shows soft-polymer flex joints 140", or living hinges, if you will. These latter two types of joints 140 are not constrained in any one plane (they are omnidirectional), and therefore provide somewhat greater flexibility to the expanded device 130 from peristaltic stomach pressures. That is, the device with omnidirectional joints 140 behaves more like a standard balloon. Again, wires or cables running through the hollow interiors of the struts can provide a directional integrity or resiliency to the otherwise relatively floppy strut.

Figure 9A:
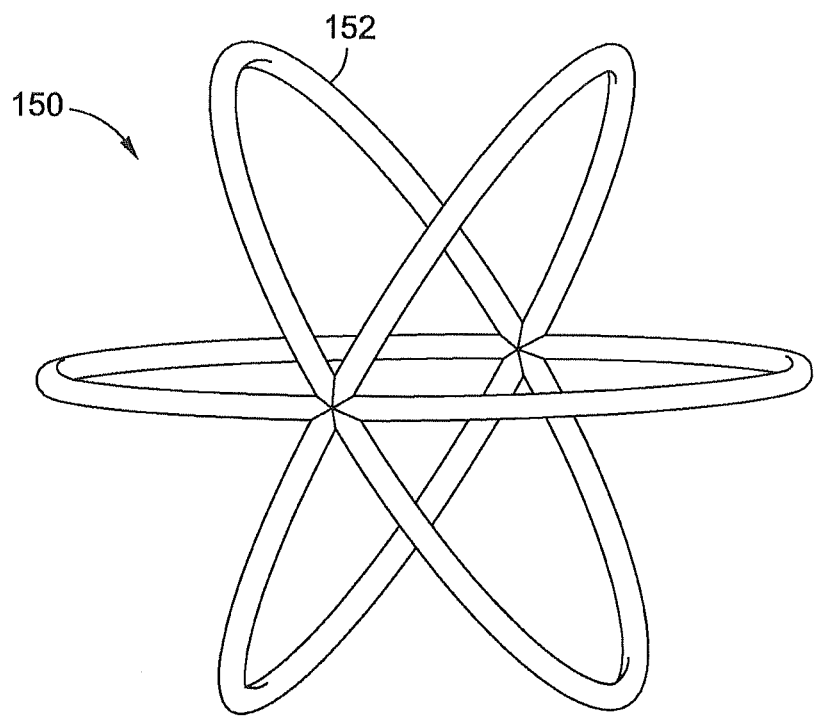
FIGS. 9A and 9B are perspective and cutaway views of an exemplary tubular wireframe intragastric device of the present application having size adjustability.
Figure 9B:
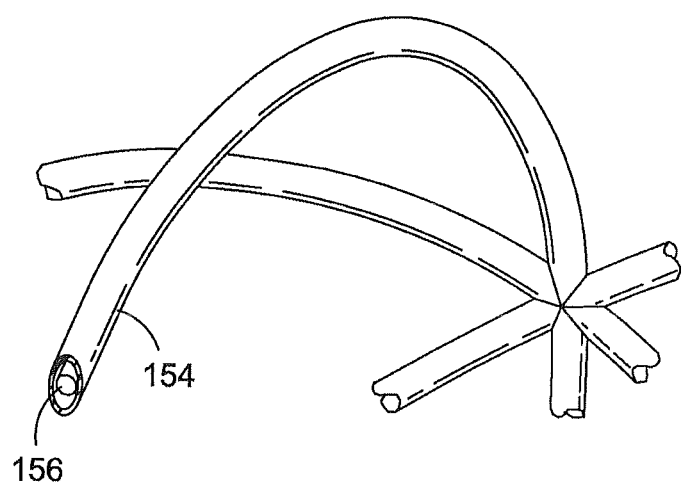

FIGS. 9A and 9B illustrate a further intragastric device 150 of the present application comprising a tubular wireframe 152 having size adjustability. The tubular wireframe 152 comprises a non-segmented frame structure without segmented strut elements, and instead includes a plurality of compliant, kink-resistant circular outer tubes 154 each with an adjustability element 156 running through the lumens. Materials for the outer tube 154 could include silicone, convoluted PTFE, or equivalent. The adjustability element 156 could be NiTi, PEEK, or other similar material with high flexibility, high tensile strength, and low elongation.

The primary difference with the device 150 of FIGS. 9A-9B is that the mechanical struts run longitudinally along the length of the structure, as opposed to being in a helical configuration. Hoop stresses of the circuited struts will allow compliance of the frame, but ensure the struts return to their default (or adjusted) position. Not shown here is an optional drape material that could envelop the frame for volume occupation purposes, as mentioned above. As with the wireframes discussed above, the flexibility and compliance of the device 150 rely on the material properties of the outer tube 154 and adjustability element 156. Providing a tubular structure with a lumen within which a metal such as Nitinol can be placed provides for greater longevity of the implant by preventing exposure of the adjustability element 156 to corrosive gastric solutions.

Figure 10:
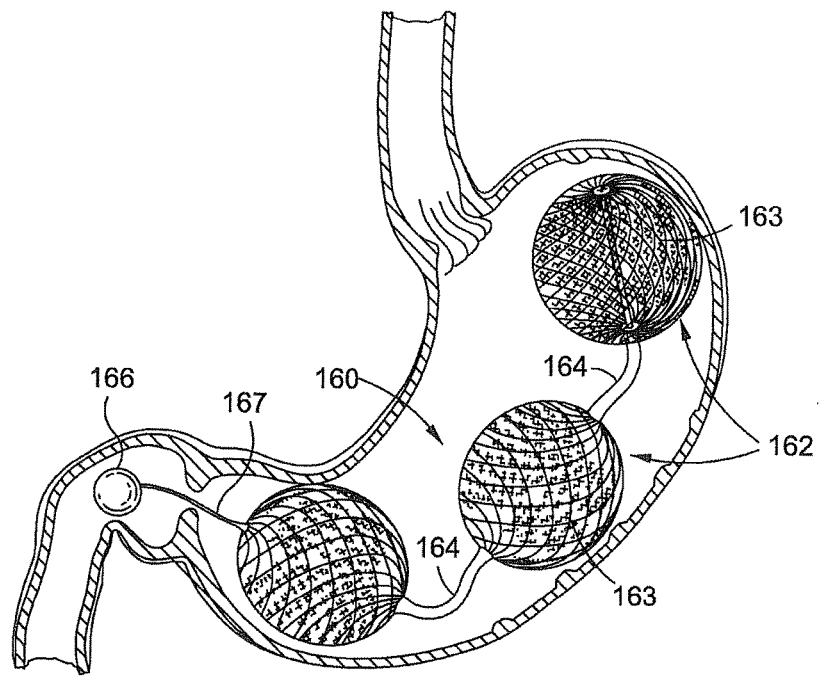
FIG. 10 shows an intragastric device including three tethered inflated balls within the stomach cavity connected to an anchor within the duodenum.

Another space-occupying satiety-inducing device 160 of the present application is shown in FIG. 10, and comprises a plurality of balls 162 linked in series and having slots or flutes 163 thereon. In the illustrated embodiment, there are three balls 162 linked by two intermediate tethers 164. The balls 162 are preferably are configured like any of the intragastric devices disclosed herein, and may be simple frames or frames draped with a mesh, although fluid such as saline may be used to fill the hollow cavities within each ball. This device 160 is intended to be placed in the stomach, transorally, without invasive surgery, and without associated patient risks of invasive surgery. Recovery time is thought to be minimal, as no extensive tissue healing is required. A one year or longer implant period is targeted, as product life span is material-dependent upon long-term survivability within acidic stomach environment.

Figure 11:
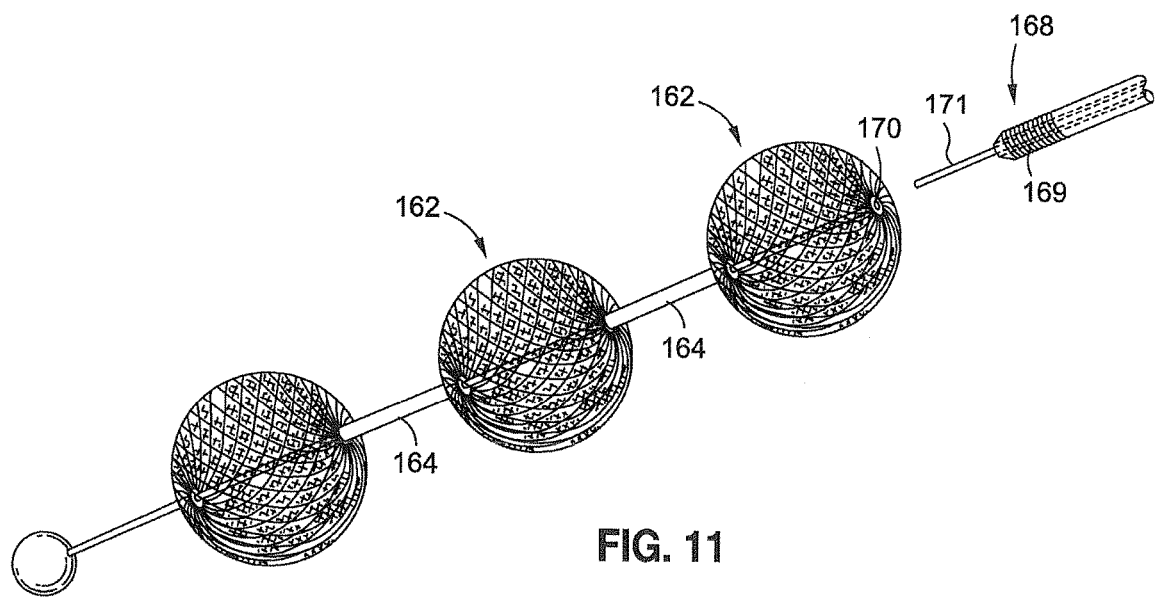
FIG. 11 is an exploded perspective view of the device of FIG. 10 and the distal end of an exemplary delivery obturator.
Figure 13:
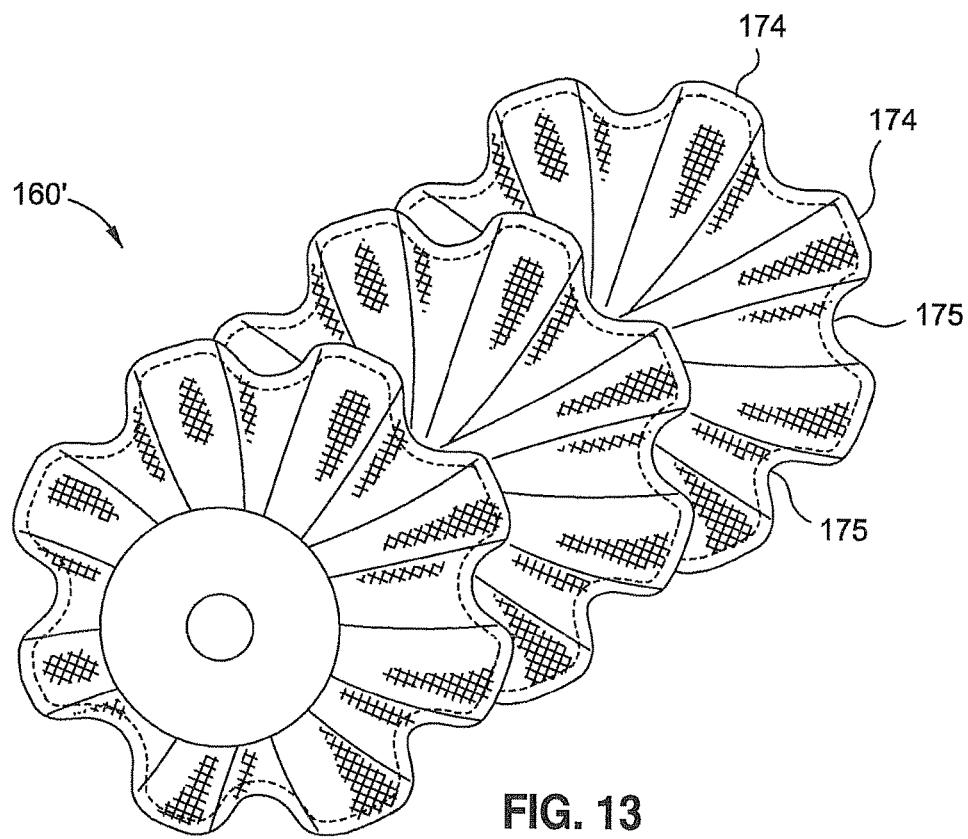
FIG. 13 shows an alternative intragastric device with three tethered inflated balls having exaggerated exterior flutes.

In addition to the embodiment shown in FIGS. 10 and 11, a number of other similar embodiments through FIG. 13 or also shown. In all cases the linked balls stimulate the stomach walls, they may occupy space in the stomach, and some of the devices 160 may also delay gastric emptying so food passing through the pylorus into the duodenum takes longer than usual. Each of these events are thought to precipitate early feelings of satiety. Through these means, additional ingestion later during any single meal is not as likely to be desired.

In the embodiment of FIGS. 10 and 11, a stainless steel ball 166 attached to the distal end of the device via a tether 167 is small enough to pass through the pyloric sphincter, but because of the size and configuration of the semi-rigid balls 162, they cannot pass through. This serves to retain the ball 166 from descending any further than the length of the tether 167 allows. The ball 166 is thus held in place in the upper duodenum, so food must pass around the ball to exit the stomach, rather than exiting freely, therefore delaying gastric emptying. The tether 167 is sufficiently thin so that the pyloric sphincter can easily close around it, and not interfere with ordinary stomach processes. It should be noted that though stainless steel is a particularly suitable material for the ball 166, it may be formed from a variety materials with sufficient mass and specific gravity that prevent it from migrating back up through the pyloric sphincter.

For insertion of the device in FIG. 10, a specially configured, temporary (removable) surgical obturator 168 is used as seen in FIG. 11. A distal end 169 of the obturator 168 threads into a threaded fitting 170 in the proximal ball 162 of the device 160. A stiff wire 171 then extends from the obturator 168 in through the series of connected balls 162. The operator pushes the wire 171 against the inside of the distal ball 162 of the device 160, thereby elongating and compressing the assembly of balls so it can fit comfortably down the esophagus. Because the balls 162 are not pressurized, they elongate to a more oval shape when the wire 171 stretches the assembly. The same principle applies to single collapsible frames as described above.

The surgeon then wends the assembly transorally down through the esophagus and into the stomach. Once in place, the wire 171 is retracted and the obturator 168 removed from the fitting 170 in the proximal ball 162, thus permitting each ball to expand. In one embodiment, the balls 162 have expanded diameters of between 30-32 mm, and may be compressed by elongation to between 9-10 mm. The weight of the stainless steel ball 166 causes it to migrate through the pyloric sphincter and "seat" in the upper duodenum, thereby anchoring the distal end of the device 160.

For device removal, the operator re-introduces the obturator 168 along with its central wire 171 down the esophagus into the stomach. Radiopaque rings surrounding both the threads in the fitting 170 of the device 160 and threads 169 of the obturator 160 guide the operator so that the mating elements can be aligned and threaded together. The operator presses the wire 171 on the inside of the distal ball 162, thereby elongating and compressing the device 160 so it can be pulled comfortably up the esophagus and out the mouth, dragging the steel ball along.

Figure 12:
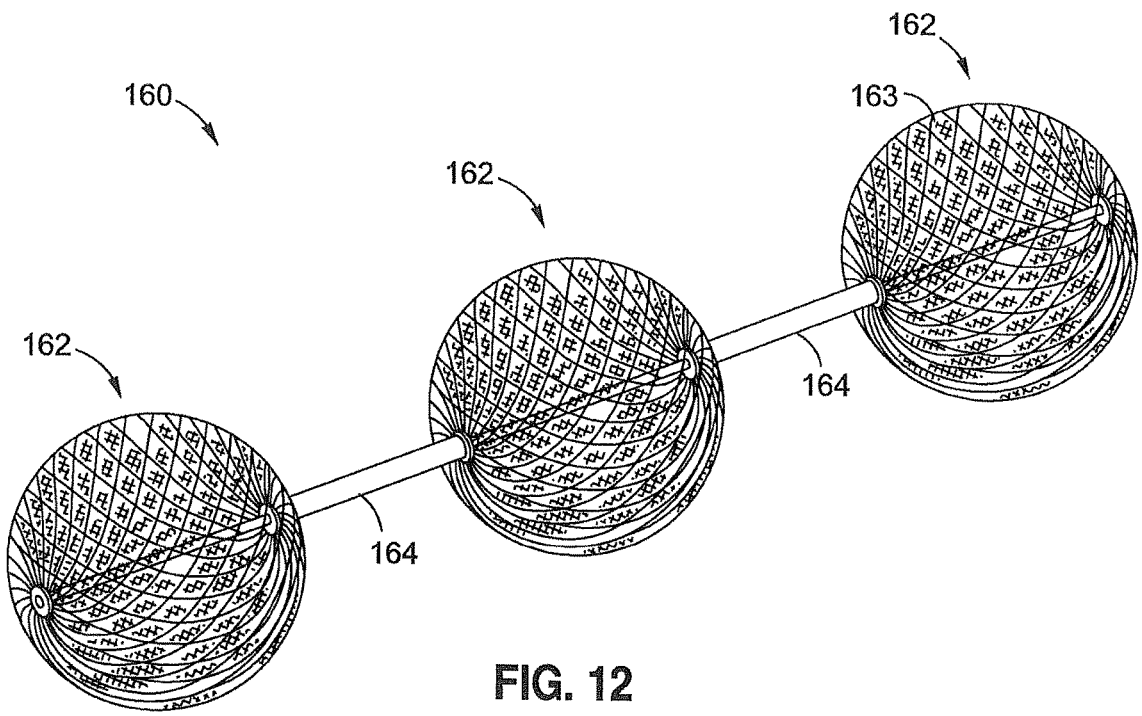
FIG. 12 shows an intragastric device with three tethered inflated balls similar to that of FIGS. 10-11 but without an anchor.

FIG. 12 illustrates a still further embodiment of the balls 162 connected in series by tethers 164. However, in this embodiment there is no distal steel ball to anchor the device in the duodenum, and thus no delayed gastric emptying. This assembly will lie anywhere in the stomach to occupy space and may exert pressure on the cardia region to promote satiety hormone release.

FIG. 13 illustrates an alternative embodiment of the series-connected balls, as in FIG. 10. The alternative device 160' features a series of balls 162' that are much like the earlier-described balls or flexible frames, but have substantially larger flutes or slots 174 separated by grooves 175. The more crenellated shape of the balls 162' helps prevent blocking of the pylorus, thus avoiding delaying gastric emptying. The relatively deep grooves in the sides of the balls 162' also permit food matter to pass between the balls and the stomach walls.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:

Silicone materials used include 3206 silicone for any shells, inflatable structures, or otherwise flexible hollow structures. Any fill valves will be made from 4850 silicone with 6% $BaSo_4$. Tubular structures or other flexible conduits will be made from silicone rubber as defined by the Food and Drug Administration (FDA) in the Code of Federal Regulations (CFR) Title 21 Section 177.2600.

Purposes:

the devices are for human implant, the devices are intended to occupy gastric space while also applying intermittent pressure to various and continually changing areas of the stomach;

the devices are intended to stimulate feelings of satiety, thereby functioning as a treatment for obesity.

General Implant Procedures:

The device is intended to be implanted transorally via endoscope into the corpus of the stomach.

Implantation of the medical devices will occur via endoscopy.

Nasal/Respiratory administration of oxygen and isoflurane to be used during surgical procedures to maintain anesthesia as necessary.

One exemplary implant procedure is listed below.

a) Perform preliminary endoscopy on the patient to examine the GI tract and determine if there are any anatomical anomalies which may affect the procedure and/or outcome of the study.

b) Insert and introducer into the over-tube.

c) Insert a gastroscope through the introducer inlet until the flexible portion of the gastroscope is fully exited the distal end of the introducer.

d) Leading under endoscopic vision, gently navigate the gastroscope, followed by the introducer/over-tube, into the stomach.

e) Remove gastroscope and introducer while keeping the over-tube in place.

f) OPTIONAL: Place the insufflation cap on the over-tubes inlet, insert the gastroscope, and navigate back to the stomach cavity.

g) OPTIONAL: Insufflate the stomach with air/inert gas to provide greater endoscopic visual working volume.

h) Collapse the gastric implant and insert the lubricated implant into the over-tube, with inflation catheter following if required.

i) Under endoscopic vision, push the gastric implant down the over-tube with gastroscope until visual confirmation of deployment of the device into the stomach can be determined.

j) Remove the guide-wire from the inflation catheter is used.

k) If inflated: Inflate the implant using a standard BioEnterics Intragastric Balloon System ("BIB System") Fill kit.

l) Using 50-60 cc increments, inflate the volume to the desired fill volume.

m) Remove the inflation catheter via over-tube.

n) Inspect the gastric implant under endoscopic vision for valve leakage, and any other potential anomalies. Record all observations.

o) Remove the gastroscope from over-tube.

p) Remove the over-tube from the patient.

End Point Criteria:

Weight Loss

Comprehensive Metabolic Panel (CMP)

HbA1C

Lipid Panel

Tissue Samples/Response

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An intragastric obesity treatment implant, comprising: a first collapsible/expandable frame formed of a first plurality of spaced struts each extending between first end poles along a generally helical path, the first frame having a size sufficient to contact the interior stomach walls upon contraction thereof, the first frame being capable of being converted into a substantially linear delivery configuration by displacing the first end poles away from one another and being formed of a material that will resist degradation over a period of at least six months within the stomach; a second collapsible/expandable frame formed of a second plurality of spaced struts each extending between second end poles along a generally helical path; and an intermediate tether connecting the first and second frames in series.

2. The implant of claim 1, further including a flexible material draped around and connected to at least one of the first and second frames so as to span across spaces between the struts of each draped frame.

3. The implant of claim 2, wherein the flexible material is a porous mesh.

4. The implant of claim 2, wherein the flexible material is impermeable and each draped frame of the implant is filled with saline.

5. The implant of claim 1, wherein the struts of each frame are discrete wires retained together at the respective end poles of each frame.

6. The implant of claim 1, wherein for each frame the respective struts are interwoven to define a sphere when relaxed.

7. The implant of claim 6, wherein the helical struts of at least one of the first frame and the second frame all wind around the sphere in one direction between the end poles, CW or CCW.

8. The implant of claim 6, wherein the helical struts of at least one of the first frame and the second frame wind around the sphere in two directions between the end poles, CW and CCW, to form a braided mesh.

9. The implant of claim 1, wherein the shape of each collapsible/expandable frame is adjustable in vivo.

10. The implant of claim 1, wherein the struts of at least one of the first frame and the second frame are Nitinol wires and the ends of the wires are held by end caps of silicone.

11. The implant of claim 1, further comprising:
a third collapsible/expandable frame formed of a third plurality of spaced struts; and
an intermediate tether between the second and third frames in series.

12. The implant of claim 1, further including a duodenal anchor connected to a distal one of the frames, the duodenal anchor having a size that permits it to pass through the pyloric sphincter and be formed of a material of sufficient mass and specific gravity that prevents it from migrating back up through the pyloric sphincter.

13. The implant of claim 1, wherein a proximal one of the frames includes an internally threaded sleeve suitable for receiving an externally threaded end of a delivery tube.

14. The implant of claim 1, wherein the intermediate tether is tubular permitting passage of a stiff rod through the series of frames.

15. The implant of claim 1, further including a flexible material draped around and connected to each of the first and second frames so as to span across the spaces between the first plurality and second plurality of struts.

16. An intragastric obesity treatment implant, comprising:
a collapsible/expandable frame formed of a plurality of spaced articulable struts each extending between end poles, the frame having a relaxed generally spherical configuration with a size sufficient to contact the interior stomach walls upon contraction thereof, the frame being capable of being converted into a substantially linear delivery configuration by displacing the poles away from one another and being formed of a material that will resist degradation over a period of at least six months within the stomach, wherein the struts include joints displaced between the end poles.

17. The implant of claim 16, further including a flexible material draped around and connected to the frame so as to span across the spaces between the struts.

18. The implant of claim 16, wherein the joints are hinges and wherein each strut is comprised of a plurality of stiff members connected together between the poles by at least one hinge.

* * * * *